(12) United States Patent
Kothandaraman et al.

(10) Patent No.: US 10,888,704 B2
(45) Date of Patent: Jan. 12, 2021

(54) FILTERING ALGORITHM FOR ASSESSING COMMUNICATIONS WIRELESSLY RECEIVED BY AN IMPLANTABLE MEDICAL DEVICE

(71) Applicant: Boston Scientific Neuromodulation Corporation, Valencia, CA (US)

(72) Inventors: Sridhar Kothandaraman, Valencia, CA (US); Dennis Zottola, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 146 days.

(21) Appl. No.: 16/353,901

(22) Filed: Mar. 14, 2019

(65) Prior Publication Data

US 2019/0209851 A1 Jul. 11, 2019

Related U.S. Application Data

(63) Continuation of application No. 15/635,453, filed on Jun. 28, 2017, now Pat. No. 10,272,251, which is a
(Continued)

(51) Int. Cl.
*A61N 1/372* (2006.01)
*A61N 1/36* (2006.01)

(52) U.S. Cl.
CPC ..... *A61N 1/37252* (2013.01); *A61N 1/36071* (2013.01); *A61N 1/37229* (2013.01); *A61N 1/37235* (2013.01)

(58) Field of Classification Search
CPC ............ A61N 1/37252; A61N 1/37229; A61N 1/37235
(Continued)

(56) References Cited

U.S. PATENT DOCUMENTS 4,365,290 A 12/1982 Nelms et al.
5,720,770 A 2/1998 Nappholz et al.
(Continued)

FOREIGN PATENT DOCUMENTS

WO 2003/095024 11/2013

OTHER PUBLICATIONS

Kothandaraman, Sridhar, "Replaceable RF Communications Card for Implantable Medical Device Programmers", Prior Art Database Technical Disclosure, pp. 1-4 (Jul. 3, 2003).
(Continued)

*Primary Examiner* — Erin M Piateski
(74) *Attorney, Agent, or Firm* — Lewis & Reese, PLLC

(57) ABSTRACT

A filtering algorithm implemented by a filtering module in an implantable medical device (IMD), or in an external device for communicating with an IMD, is disclosed which reviews blocks based on a number of rules. The filtering module preferably comprises both firewall and instruction analysis modules. The instruction analysis module analyzes the instructions and associated data (if present) in each block to determine whether such blocks would compromise operation of the IPG or injure a patient if executed. Instruction rules corresponding to an instruction identified in the block are retrieved by the instruction analysis module. The instruction analysis module reviews the block per the retrieved rules, and possibly also in light of current and historical IPG therapy setting or mode data, or other received but unexecuted blocks. If a block is compliant, it is executed by the IMD or transmitted to the IMD.

18 Claims, 13 Drawing Sheets

Related U.S. Application Data continuation of application No. 14/470,756, filed on Aug. 27, 2014, now Pat. No. 9,717,919.

(60) Provisional application No. 61/874,916, filed on Sep. 6, 2013.

(58) Field of Classification Search
USPC .......................................................... 607/59
See application file for complete search history.

(56) References Cited

U.S. PATENT DOCUMENTS

| | | | |
|---|---|---|---|
| 5,759,199 A | 6/1998 | Snell et al. | |
| 6,035,050 A | 3/2000 | Weinfurtner et al. | |
| 6,219,580 B1 | 4/2001 | Faltys et al. | |
| 6,250,309 B1 | 6/2001 | Krichen et al. | |
| 6,434,429 B1 | 8/2002 | Kraus et al. | |
| 6,442,432 B2 | 8/2002 | Lee | |
| 6,490,487 B1 | 12/2002 | Kraus et al. | |
| 6,497,655 B1 | 12/2002 | Linberg et al. | |
| 6,516,227 B1 | 2/2003 | Meadows et al. | |
| 6,553,262 B1 | 4/2003 | Lang et al. | |
| 6,574,509 B1 | 6/2003 | Kraus et al. | |
| 6,622,045 B2 | 9/2003 | Snell et al. | |
| 6,662,052 B1 | 12/2003 | Sarwal et al. | |
| 6,738,671 B2 | 5/2004 | Christophersom et al. | |
| 7,043,305 B2 | 5/2006 | KenKnight et al. | |
| 7,060,030 B2 | 6/2006 | Von Arx et al. | |
| 7,191,012 B2 | 3/2007 | Boveja et al. | |
| 7,313,529 B2 | 12/2007 | Thompson | |
| 7,369,897 B2 | 5/2008 | Boveja et al. | |
| 7,742,821 B1 | 6/2010 | Vamos et al. | |
| 7,801,602 B2 | 9/2010 | McClure et al. | |
| 7,848,819 B2 | 12/2010 | Goetz et al. | |
| 7,865,242 B2 | 1/2011 | Diebold et al. | |
| 7,885,712 B2 | 2/2011 | Goetz et al. | |
| 7,978,062 B2 | 7/2011 | LaLonde et al. | |
| 8,002,700 B2 | 8/2011 | Ferek-Petric et al. | |
| 8,103,346 B2 | 1/2012 | Mass et al. | |
| 8,130,093 B2 | 3/2012 | Mazar et al. | |
| 8,140,160 B2 | 3/2012 | Pless et al. | |
| 8,174,395 B2 | 5/2012 | Samuelsson et al. | |
| 8,265,757 B2 | 9/2012 | Mass et al. | |
| 8,373,556 B2 | 2/2013 | LaLonde et al. | |
| 8,395,498 B2 | 3/2013 | Gaskill et al. | |
| 8,410,940 B2 | 4/2013 | Samuelsson et al. | |
| 2003/0114897 A1 | 6/2003 | Von Arx | |
| 2003/0144711 A1 | 7/2003 | Pless | |
| 2004/0044372 A1 | 3/2004 | Bocek | |
| 2004/0088374 A1 | 5/2004 | Webb et al. | |
| 2005/0049656 A1 | 3/2005 | Peterson | |
| 2005/0283210 A1* | 12/2005 | Blischak | A61M 5/14276 607/60 |
| 2006/0094970 A1 | 5/2006 | Drew | |
| 2007/0123946 A1 | 5/2007 | Masoud | |
| 2007/0173890 A1* | 7/2007 | Armstrong | A61N 1/37252 607/2 |
| 2007/0213789 A1 | 9/2007 | Nolan et al. | |
| 2008/0046039 A1* | 2/2008 | Corndorf | A61N 1/37254 607/60 |
| 2008/0208292 A1 | 8/2008 | Persen et al. | |
| 2009/0024179 A1 | 1/2009 | Dronov | |
| 2009/0112281 A1 | 4/2009 | Miyazawa et al. | |
| 2009/0131995 A1 | 5/2009 | Sloan | |
| 2009/0210798 A1 | 8/2009 | Wu et al. | |
| 2009/0292340 A1 | 11/2009 | Mass | |
| 2010/0114208 A1 | 5/2010 | Donofrio | |
| 2010/0229324 A1 | 9/2010 | Conrad | |
| 2010/0305663 A1 | 12/2010 | Aghassian | |
| 2010/0318159 A1 | 12/2010 | Aghassian et al. | |
| 2011/0071597 A1 | 3/2011 | Aghassian | |
| 2011/0112611 A1 | 5/2011 | Aghassian | |
| 2012/0197323 A1 | 8/2012 | Elferri | |
| 2012/0197351 A1 | 8/2012 | Olson | |
| 2012/0215285 A1 | 8/2012 | Tahmasian et al. | |
| 2012/0221067 A1 | 8/2012 | Edlund | |
| 2012/0278760 A1* | 11/2012 | Cerny | A61B 5/0031 715/810 |
| 2012/0316612 A1 | 12/2012 | Warren | |
| 2013/0007210 A1 | 1/2013 | Mass et al. | |
| 2013/0073005 A1 | 3/2013 | Aghassian | |
| 2013/0076535 A1 | 3/2013 | Sievert et al. | |
| 2013/0110190 A1 | 5/2013 | Cho | |
| 2013/0116751 A1 | 5/2013 | Moffitt | |
| 2013/0172774 A1 | 7/2013 | Crowder | |
| 2014/0188193 A1 | 7/2014 | Vamos et al. | |
| 2014/0343628 A1 | 11/2014 | Kaula | |

OTHER PUBLICATIONS

"MSP430 Ultra-Low-Power Microcontrollers," Texas Instruments, Inc. (2014).

\* cited by examiner

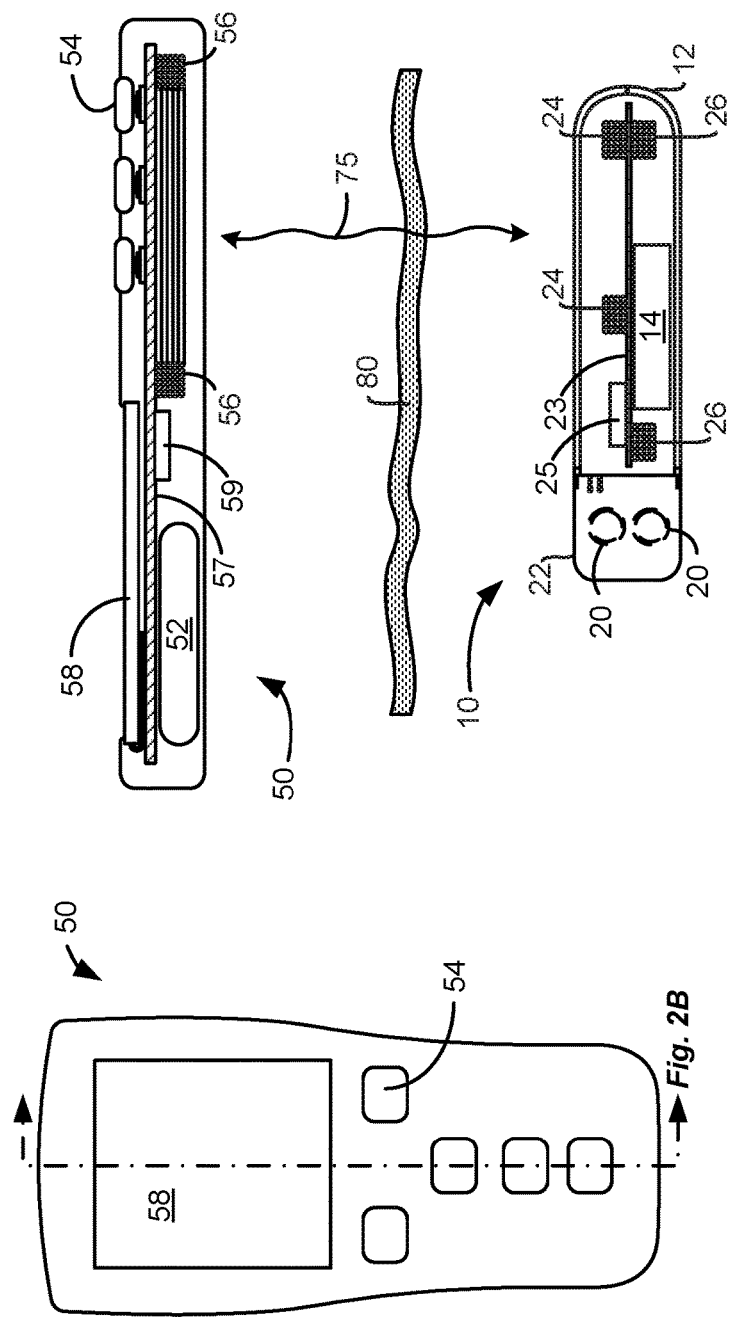
*Figure 2A (prior art)*
*Figure 2B (prior art)*
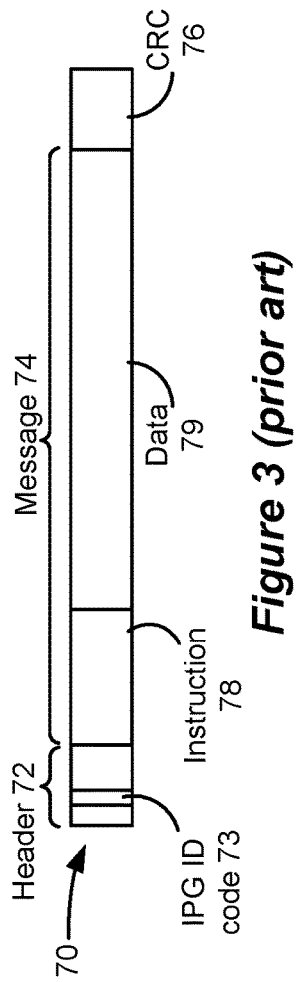
*Figure 3 (prior art)*

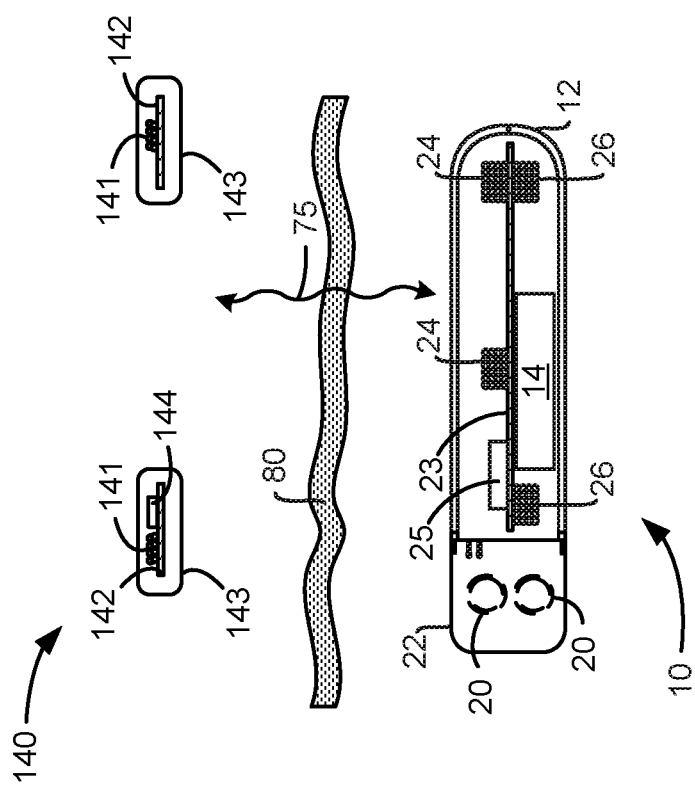
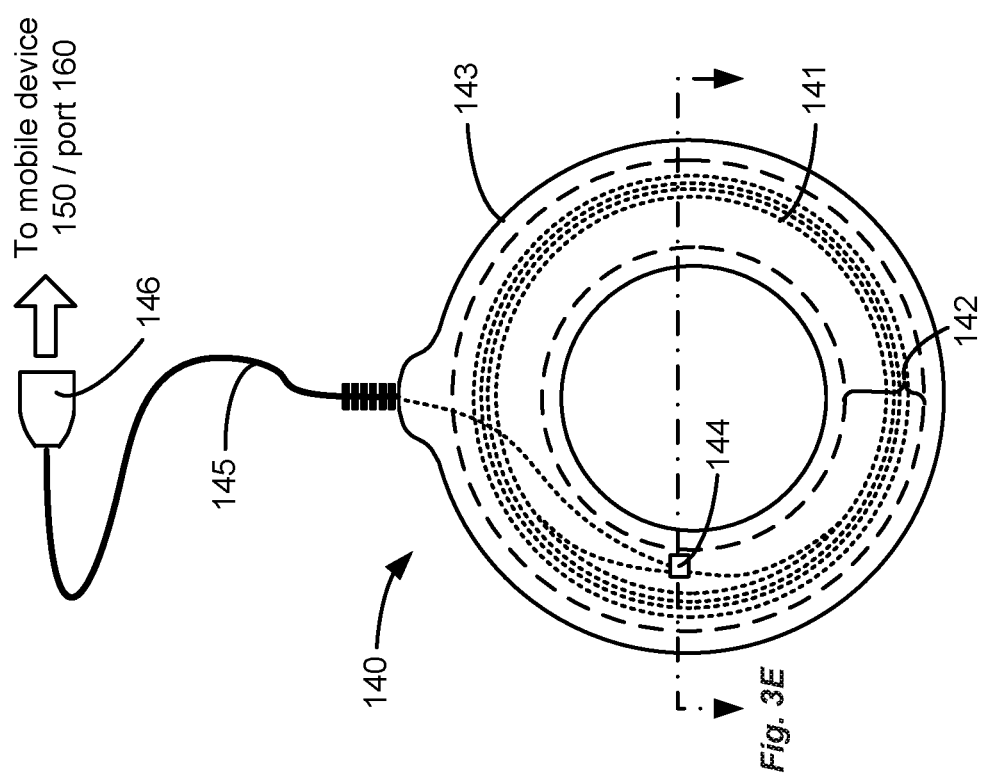
*Figure 4E*
*Figure 4D*

— 261

| Therapy setting rules 262 |
|---|
| Limit intensity increase to 5% |
| Limit intensity increase to 25% over 1 minute |
| Limit intensity to 15 mA |
| Limit intensity decrease to 20% |
| Limit intensity decrease to 50% over 10 seconds |
| Limit frequency / duration change to 10% |
| Do not allow therapy setting changes if IPG in power down mode |
| Limit active electrode change to an adjacent eletrode |
| Do not activate electrode E8 |
| *Do not activate change frequency or duration if succeeding block received within one second changes intensity* |
| *Do not increase intensity if preceding block within 0.5 seconds decreases intensity* |
| *Do not change therapy settings if any preceding block places IPG is in program mode* |

⋮

| Mode rules 263 |
|---|
| Do not place in power down mode if IPG battery > 3.0V |
| Do not place IPG in mode X if Y |
| Do not place IPG in mode Z if therapy settings equal W |
| Do not place IPG in mode A if IPG in mode B |
| Do not telemeter data from IPG in mode J |
| *Do not allow IPG mode change if preceding and succeeding block within 0.5 seconds comprises a therapy setting* |

FILTERING ALGORITHM FOR ASSESSING COMMUNICATIONS WIRELESSLY RECEIVED BY AN IMPLANTABLE MEDICAL DEVICE

CROSS-REFERENCE TO RELATED APPLICATIONS

This is a continuation of U.S. patent application Ser. No. 15/635,453, filed Jun. 28, 2017 (now allowed), which is a continuation of U.S. patent application Ser. No. 14/470,756, filed Aug. 27, 2014 (now U.S. Pat. No. 9,717,919), which is a non-provisional of U.S. Provisional Patent Application Ser. No. 61/874,916, filed Sep. 6, 2013. Priority is claimed to these applications, and they are incorporated herein by reference in their entireties.

FIELD OF THE INVENTION

The present invention relates generally to implantable medical device systems.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

As shown in FIG. 1, an SCS system typically includes an Implantable Pulse Generator (IPG) 10, which includes a biocompatible device case 12 formed of titanium, for example. The case 12 typically holds the circuitry and battery 14 necessary for the IPG to function. The IPG 10 is coupled to electrodes 16 via one or more electrode leads 18 (two of which are shown). The electrodes 16 are coupled to the IPG 10 at one or more lead connectors 20 fixed in a header 22, which can comprise an epoxy for example. In the illustrated embodiment there are sixteen electrodes, although the number of leads and electrodes is application specific and therefore can vary. In an SCS application, two electrode leads 18 are typically implanted on the right and left side of the dura within the patient's spinal cord. The proximal ends of the leads 18 are then tunneled through the patient's flesh to a distant location, such as the buttocks, where the IPG case 12 is implanted, at which point they are coupled to the lead connector(s) 20.

FIG. 2A shows a front view of an external controller 50 for communicating with the IPG 10, and FIG. 2B shows the external controller 50 and IPG 10 in cross section. Two coils (antennas) are generally present in the IPG 10: a telemetry coil 24 used to transmit/receive data via a wireless communications link 75 to/from the external controller 50; and a charging coil 26 for charging or recharging the IPG's battery 14 using an external charger (not shown). These and other components 25 necessary for IPG operation are electrically coupled to a circuit board 23. The telemetry coil 24 can be mounted within the header 22 of the IPG 10, or can be located within the case 12 as shown.

The external controller 50, such as a hand-held programmer or a clinician's programmer, is used to send or adjust the therapy settings that the IPG 10 will provide to the patient (such as which electrodes 16 are active, whether such electrodes sink or source current (polarity), and the duration, frequency, and amplitude (intensity) of pulses formed at the electrodes, etc.). The external controller 50 can also act as a receiver of data from the IPG 10, such as various data reporting on the IPG's status and the level of the IPG 10's battery 14. The external controller 50 is itself powered by a battery 52, but could also be powered by plugging it into a wall outlet for example. A user interface similar to that used for a cell phone is provided to operate the external controller 50, including buttons 54 and a display 58. The external controller 50 also includes a telemetry coil 56. These and other components 59 necessary for IPG operation are electrically coupled to a circuit board 57.

Wireless data transfer between the IPG 10 and the external controller 50 typically takes place via magnetic inductive coupling between coils 24 and 56, each of which can act as the transmitter or the receiver to enable two-way communication between the two devices. A Frequency Shift Keying (FSK) protocol can be used to send data between the two coils 24 and 56 via link 75. Although use of an FSK protocol in legacy systems is discussed below, use of this protocol is not universal, and other protocols employing different forms of modulation can be used to communicate between an external controller and an IPG, as one skilled in the art understands. Telemetry of data can occur transcutaneously though a patient's tissue 80.

Historically, external medical devices such as external controller 50 have been built by the manufacturer of the IPGs, and thus such external devices are generally dedicated to only communicate with such IPGs. The inventors have realized that there are many commercial mobile devices, such as mobile cell phones and multi-function tablets, that have the necessary configurable hardware and software to function as an external controller for an IPG or other implantable medical device. Using such mobile devices as external controllers for an implantable medical device would benefit both manufacturers and end users: manufacturers would not need to build dedicated external controllers that end users must buy, and end users could control their IPGs without the inconvenience of having to carry additional custom external controllers.

However, there are problems with this solution. Mobile devices are often configured with necessary hardware and software to communicate with other devices using short-range protocols, such as Bluetooth, Bluetooth Low Energy (BLE), Near Field Communication (NFC), Zigbee, and WiFi, as well as by using long-range cellular telephony protocols, any of which can be used to ultimately wirelessly connect the mobile device to the Internet or other network. While such communication channels allow for communication with an implantable medical device, they also render mobile devices less secure than traditional dedicated external controllers, particularly because they are prone to cyber attack, to computer viruses or malware, or to other intentional forms corruption. The multi-functional nature of mobile devices also makes them more prone to unintentional corruption, as their complicated nature may simply cause them to function improperly, even if they have not been intentionally corrupted. Thus, if mobile devices are used as medical devices to communicate with implantable devices, there is an increased risk that the implantable medical device could be mis-programmed and potentially injure a patient.

Implantable medical devices currently employ some level of security to determine whether communications it receives are valid and should be executed to change its operation. In this regard, it has been known in the art of IPGs to use ID codes and error codes, such as is illustrated in FIG. 3. As shown, data is telemetered from an external controller 50 to the IPG 10 in the form of a block 70, or in a series of blocks 70 in a longer, more-complicated communication session. A block 70 typically comprises a header 72, a message 74, and an error code 76 in sequence. The header 72 may include code understood by the IPG 10 as indicative of the beginning of a block 70, and may include other information such as the length or type of the message 74 to follow. The header 72 may also include an ID code 73 or address for the implantable medical device, and may also include an ID code for the external controller (not shown).

Message 74 comprises the main data "payload" of the block 70, which may further be divided into an instruction 78 and data 79 associated with that instruction. For example, instruction 78 might comprise an instruction to set or adjust therapy, with data 79 reflecting the particular settings to be set or adjusted (e.g., active electrodes, polarity, duration, frequency, intensity, etc.). Or instruction 78 might comprise an instruction for a particular therapy setting (e.g., to change, increase or decrease intensity), with data 79 reflecting the data for that therapy adjustment (e.g., the magnitude of the intensity, or a magnitude of an adjustment to the intensity).

An instruction 78 may also be unaccompanied by data 79, and an instruction 78 may cause other changes in the IPG 10 that when executed will not (directly) change therapy settings. For example, an instruction 78 may simply place the IPG 10 into a particular operational mode, such as a power down mode for power savings, a mode to ready the IPG for programming of new operation software, or to activate its telemetry circuitry to telemeter data back to the external controller 50, etc. For such instructions, accompanying data 79 may not be necessary. Message 74 may comprise multiple instructions 78, and/or multiple instructions 78/data 79 pieces, within a block 70, and message 74 can comprise a fixed or variable number of bytes.

The error code 76 appended to the end of the block 70 is used by the IPG 10 to determine whether the block has been corrupted during transmission, by electromagnetic interference for example. In the example shown in FIG. 3, the error code 76 comprises a Cyclic Redundancy Code (CRC). CRCs are well known, and are only briefly explained. A CRC is computed at the external controller 50 by dividing the block (i.e., the hexadecimal number comprising the header 72 plus the message 74) by a particular hexadecimal polynomial. The external controller 50 appends this CRC as the error code 76 to the block 70, which is transmitted to the IPG 10. On the receiving end, the IPG 10 likewise assesses the block (72 and 74) and computes a CRC using the same polynomial. If the CRC computed by the IPG 10 does not match the received CRC, the IPG will deduce that a transmission error occurred, e.g., a logic '0' bit was inadvertently received as a '1' bit, etc. In response, the IPG 10 can take appropriate action, such as discarding the block 70, or requesting the external controller 50 to resend that block.

If this error check passes at the IPG 10, the IPG 10 will next review the ID code 73 to ensure that the block 70 it received was truly intended for it. The IPG 10 may do this by comparing the received ID code 73 with an ID code stored, for example, in its memory. If the received ID code 73 does not match, the IPG 10 can take appropriate action, such as discarding the block 70.

If both the error check and ID code check pass, the block is deemed valid and the IPG 10 will accept and execute the block 70, such as by changing the stimulation intensity. It should be noted that review of the error codes and ID codes can occur in the opposite order, with the IPG 10 reviewing the ID code first and then the error code. Also, ID and error codes can likewise be employed when blocks are transmitted from the IPG 10 to the external controller 50 to allow the external controller 50 to determine whether blocks it receives from the IPG 10 are valid.

While ID codes and error codes provide some level of protection to prevent implantable medical devices from executing invalid blocks, they may not be sufficient, particularly given the potential use of more-easily-corruptible mobile devices as external controllers. For example, a corrupted mobile device could send a corrupt block containing an undesired instruction, or instruction with undesired data with or without patient intervention. Such a corrupt block could still be properly formatted at the mobile device, and could contain both a proper ID and an error. As such, this corrupt block would be deemed valid and executed at the implantable medical device, undesirably modifying operation of the implantable medical device potentially in a manner unsuitable for the patient. In an IPG, such improper operation could comprise an improper therapy setting, entry into an improper operational mode, etc.

Particularly if mobile devices are used as external controllers to communicate with implantable medical devices, the inventors believe that further security measures should be taken, preferably within implantable medical devices themselves, to protect against execution of potentially-corrupt communications they may receive.

BRIEF DESCRIPTION OF THE DRAWINGS

FIGS. 2A and 2B show an external controller and the manner in which it communicates with the IPG in accordance with the prior art.

FIG. 3 shows the format of a block received at the IPG in accordance with the prior art, and the use of error codes to protect the IPG from transmission errors.

FIGS. 4B-4F show manners in which the mobile device can wirelessly communicate with the IPG.

DETAILED DESCRIPTION

A filtering algorithm implemented by a filtering module in an implantable medical device, or an external device that communicate with an implantable medical device, is disclosed which reviews blocks wirelessly received from an external device, and reviews them based on a number of rules. The filtering module preferably comprises both firewall and instruction analysis modules. The firewall module can reject blocks based on one or more of packet, stateful, or application filtering rules. The instruction analysis module analyzes the instructions and data (if present) in each block to determine whether such blocks would compromise operation of the IPG or injure a patient if executed. The instruction in the block (e.g., an implant therapy setting instruction or an implant operational mode instruction) is identified, and one or more instruction rules corresponding to that instruction are retrieved by the instruction analysis module. The instruction analysis module reviews the block per the retrieved rules, and possibly also in light of current and historical implant therapy settings or implant mode data, or other received but un-executed blocks. If a block is compliant, it is executed by or transmitted to the implant.

Because the filtering module implementing the filtering algorithm can be within the implantable medical device, it is secure and thus protects the implant independent of any security measures that might be used in external devices with which the implant communicates. However, the filtering algorithm could also be implemented in external devices as well, such as mobile devices, legacy external controllers, or bridge devices between the external device and the implant, as discussed further below.

Because development of the disclosed filtering algorithm was inspired by the potential use of mobile devices as external controllers for an implantable medical device, examples in which a mobile device can communicate with an implantable medical device are first discussed with reference to FIGS. 4A-4F. Details of the filtering algorithm are then explained with reference to FIGS. 7A-7C as used in an implantable medical device, and to FIGS. 8A-8B as used in an external device.

Figure 1:
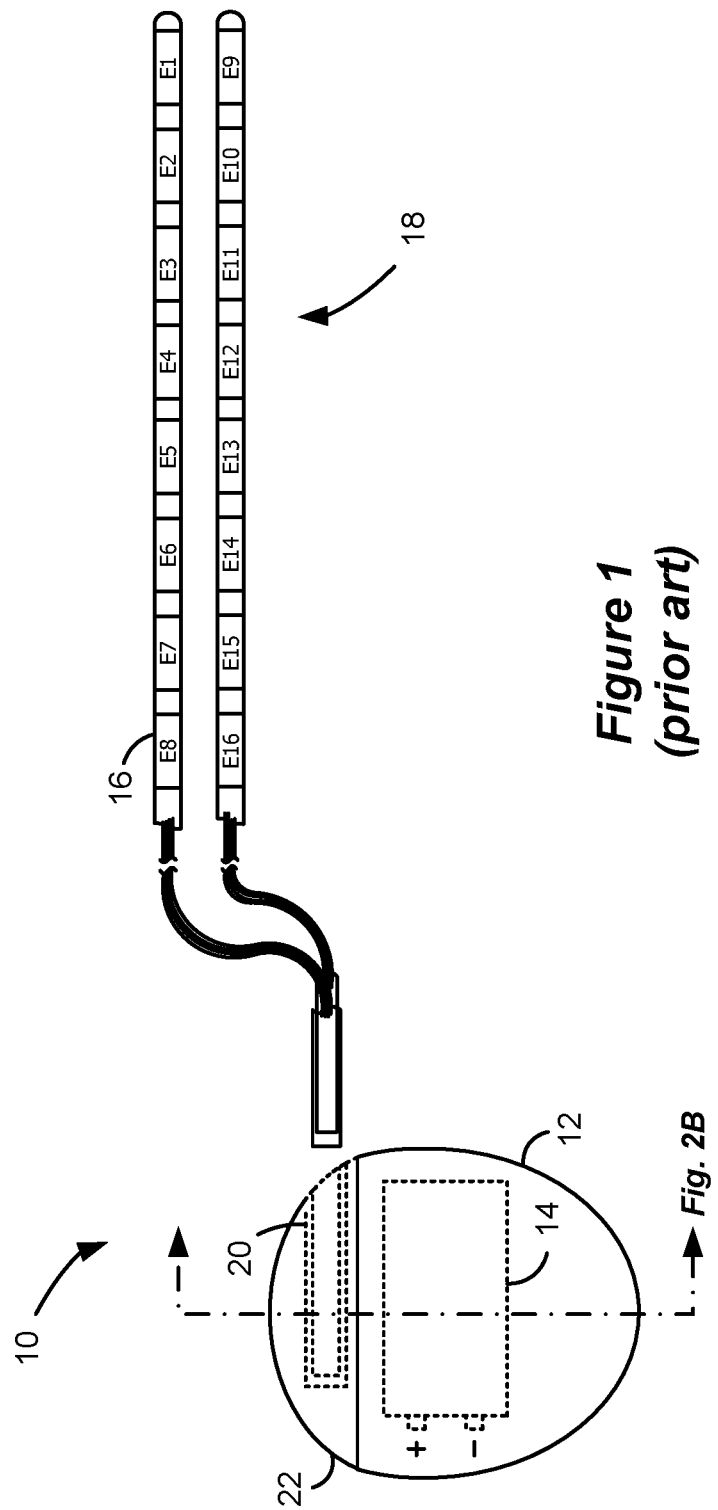
FIG. 1 shows an implantable pulse generator (IPG) in accordance with the prior art.
Figure 4B:
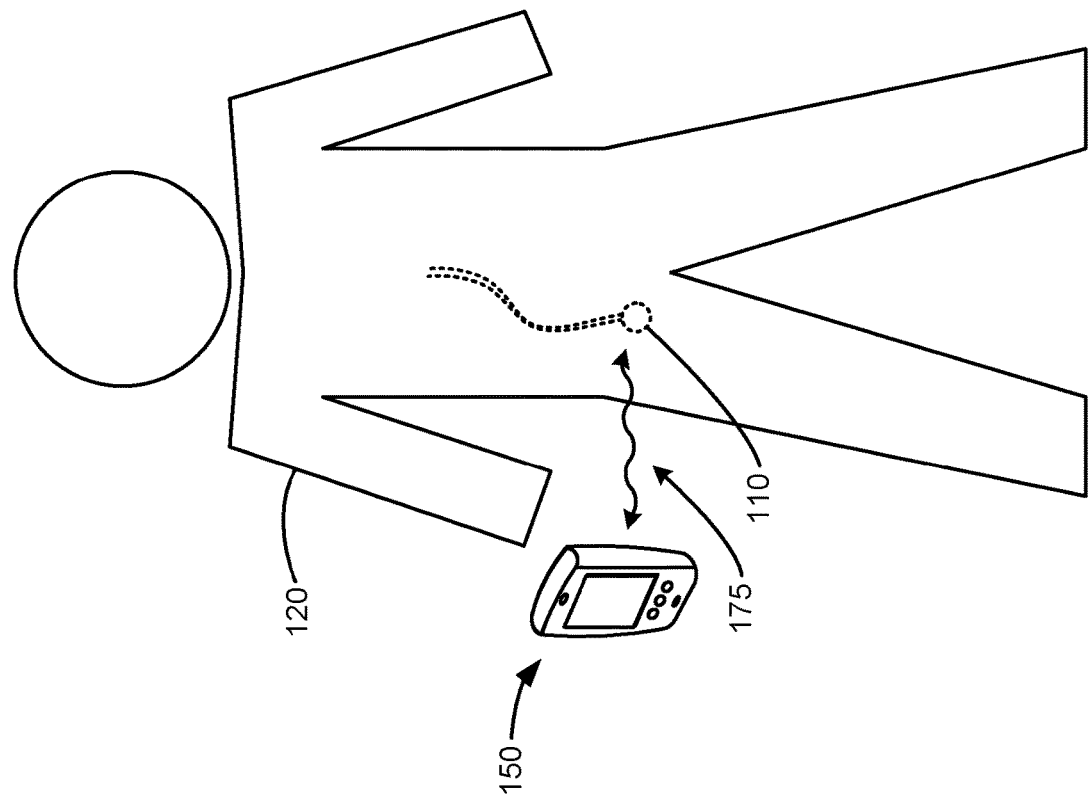
Figure 4A:
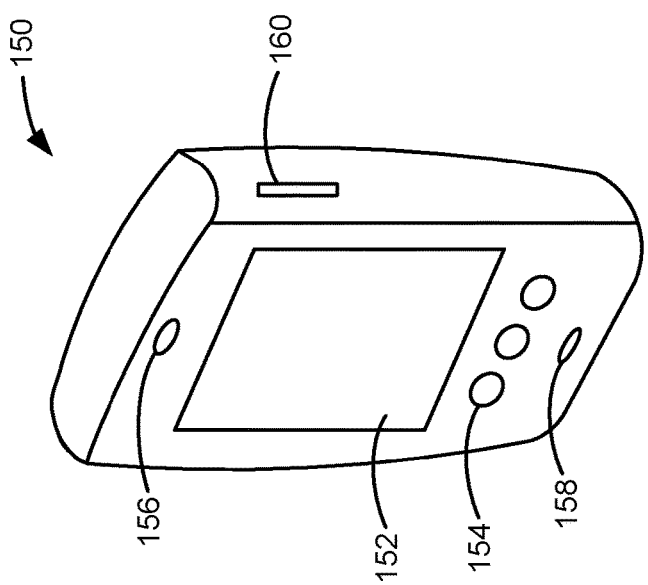
FIG. 4A shows a mobile device in accordance with an embodiment of the present invention.

FIG. 4A shows a mobile device 150, and FIG. 4B shows the mobile device 150 in communication with an IPG 110 implanted in a patient 120, in accordance with an aspect of the invention. The mobile device 150 may be a commercial, multipurpose, consumer device, such as a cell phone, tablet, personal data assistant, laptop or notebook computer, or like devices—essentially any mobile, hand-holdable device capable of functioning as an external controller for an implantable medical device. Examples include the Apple iPhone or iPad, Microsoft Surface, Nokia Lumia devices, Samsung Galaxy devices, or Google Android devices, for example.

Among other components and circuitry which will be described in further detail later, the mobile device 150 has a user interface. For example, mobile device 150 may have a display 152 for displaying information. Display 152 may also receive input from a user if it is a touch screen that receives input from a finger or stylus. The mobile device 150 may also have buttons 154 for receiving input from the user, a speaker 156, and a microphone 158. The mobile device 150 may have one or more external ports 160, such as a USB port for example, to connect the mobile device 150 to other devices, to chargers for the mobile device's battery 155 (FIG. 4C), to other computer systems, to memory cards, sticks, to systems, or to various dongles, etc.

As noted earlier, mobile devices 150 may be enabled to communicate with other devices using short-range protocols, such as Bluetooth, BLE, NFC, Zigbee, and WiFi, as well as by using long-range cellular telephony protocols. IPG 110 is modified in accordance with an aspect of the invention to directly communicate with the mobile device 150 using one of the mobile device 150's short-range protocols along wireless link 175.

Figure 4C:
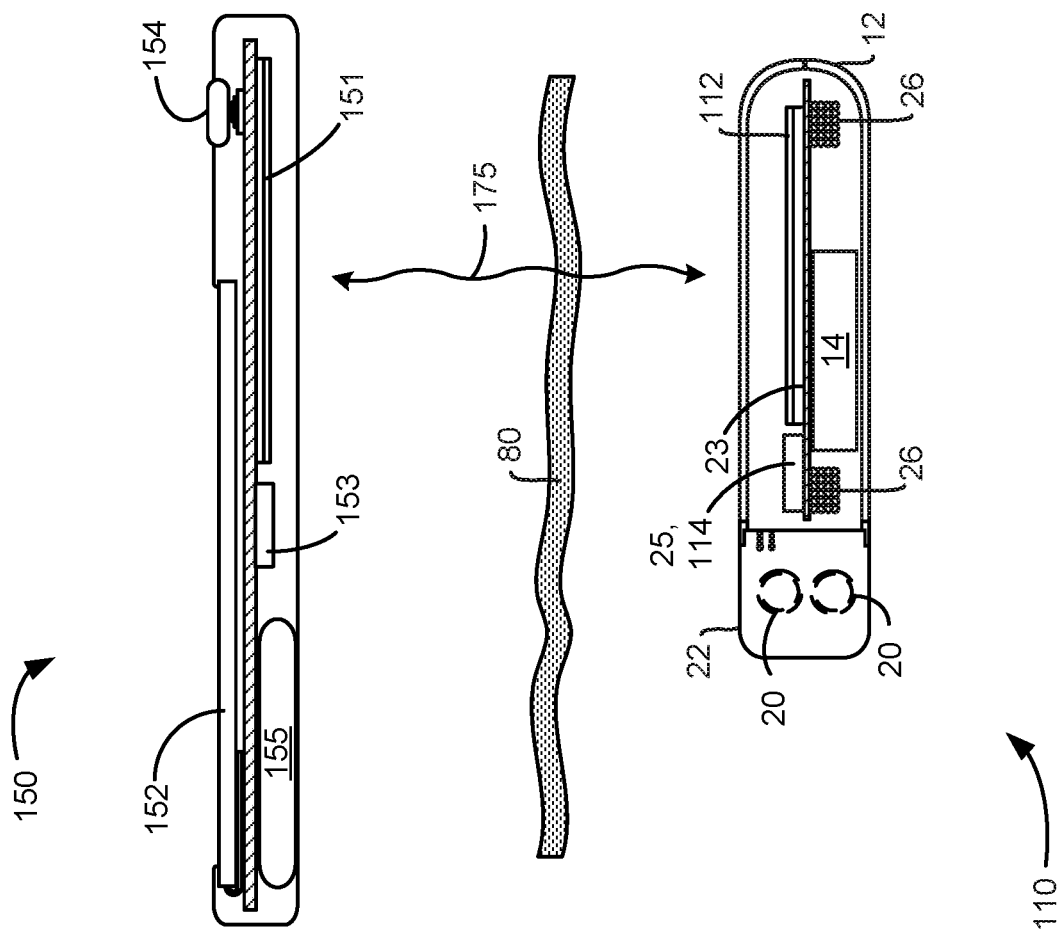

Such means of communication may use an NFC protocol, and as shown in FIG. 4C, the mobile device 150 contains NFC telemetry circuitry 153 (which comprises part of the circuitry used to operate the mobile device 150) and an NFC antenna 151 as is typical, while the IPG 110 is modified from the IPG 10 described earlier (FIG. 2B) to include NFC telemetry circuitry 114 (part of circuitry 25) and an NFC antenna 112. As with the coil-based inductive telemetry scheme discussed for IPG 10 earlier, NFC uses magnetic inductive coupling, and thus NFC antennas 151 and 112 comprise loop antennas. Such loop antennas may be formed as a spiral in a circuit board, such as a flexible Kapton film, as opposed to traditional copper wire windings. Modulation and demodulation of data at the telemetry circuitries 153 and 114 may occur using Miller coding or Manchester encoding, for example.

NFC operates within the unlicensed Industrial Scientific and Medical (ISM) band at 13.56 MHz. NFC is preferred for IPG communications because its lower frequency will not be as attenuated in the patient's tissue 80 as will the higher frequencies used for other short-range protocols. But NFC also operates at shorter distances, at less than 0.2 meters, for example. Still, this is suitable as the mobile device 150 can be held relatively close to the IPG 110 during a communication session. Use of NFC to communicate between the mobile device 150 and the IPG 110, however, is not strictly necessary, and the IPG 110 can instead include an antenna and circuitry to match other short-range protocols enabled by the mobile device 150.

As shown in FIG. 4C, the IPG 110 no longer contains a telemetry coil 24 (FIG. 2B), because the communication link 175 between the mobile device 150 and the IPG 110 does not occur using legacy FSK communications. However, this is not strictly necessary, and the IPG 110 could still retain its telemetry coil 24 to allow it to communicate with a legacy external controller (FIG. 2A, 50) using FSK.

Alternatively, a legacy FSK communication link 75 can be used between the mobile device 150 and an (unmodified) IPG 10 (FIG. 2B), and a first example is shown in FIGS. 4D and 4E. In this example, a telemetry coil assembly 140 is used as an intermediary between the mobile device 150 and the IPG 10. The coil assembly 140 includes a telemetry coil 141 similar to the coil 56 used in the legacy external controller 50 (FIG. 2B), which coil 141 is mounted to a circuit board 142. Also mounted to the circuit board 142 is FSK telemetry circuitry 144, similar to that included as one of the components 59 of legacy external controller 50 (FIG. 2B). The telemetry coil 141, circuit board 142, and FSK telemetry circuitry 144 are contained within a coil housing 143. A cable 145 couples the FSK telemetry circuitry 144 to a connector 146, which couples to a port (e.g., port 160; FIG. 4A) on the mobile device 150. Port 160 can both provide power to the FSK telemetry circuitry 144 and send and receive a string of digital data bits to and from the FSK telemetry circuitry. The FSK telemetry circuitry 144 may include amplifiers and other circuitry to modulate digital data bits sent from the mobile device 150 via port 160 and connector 146, and to activate the coil 141 to send FSK modulated data to the IPG 10 via link 75. The FSK telemetry circuitry 144 also may include amplifiers and other circuitry to demodulate FSK modulated data transmitted from the IPG 10 via link 75 and received at coil 141, and to provide such demodulated data as a string of digital data bits to the mobile device 150 via connector 146/port 160. The mobile device 150 can enable port 160 to send and receive the digital data bits when the mobile device 150 is configured for use as a medical device for communicating with the IPG 10, as will be explained in detail later. In this embodiment, the coil assembly 140 can be placed proximate to the IPG 10 (such as in a belt with a pocket), while the mobile device 150 can remain relatively distant from the IPG 10 by virtue of the length of cable 145, which is convenient for the user.

Figure 4F:
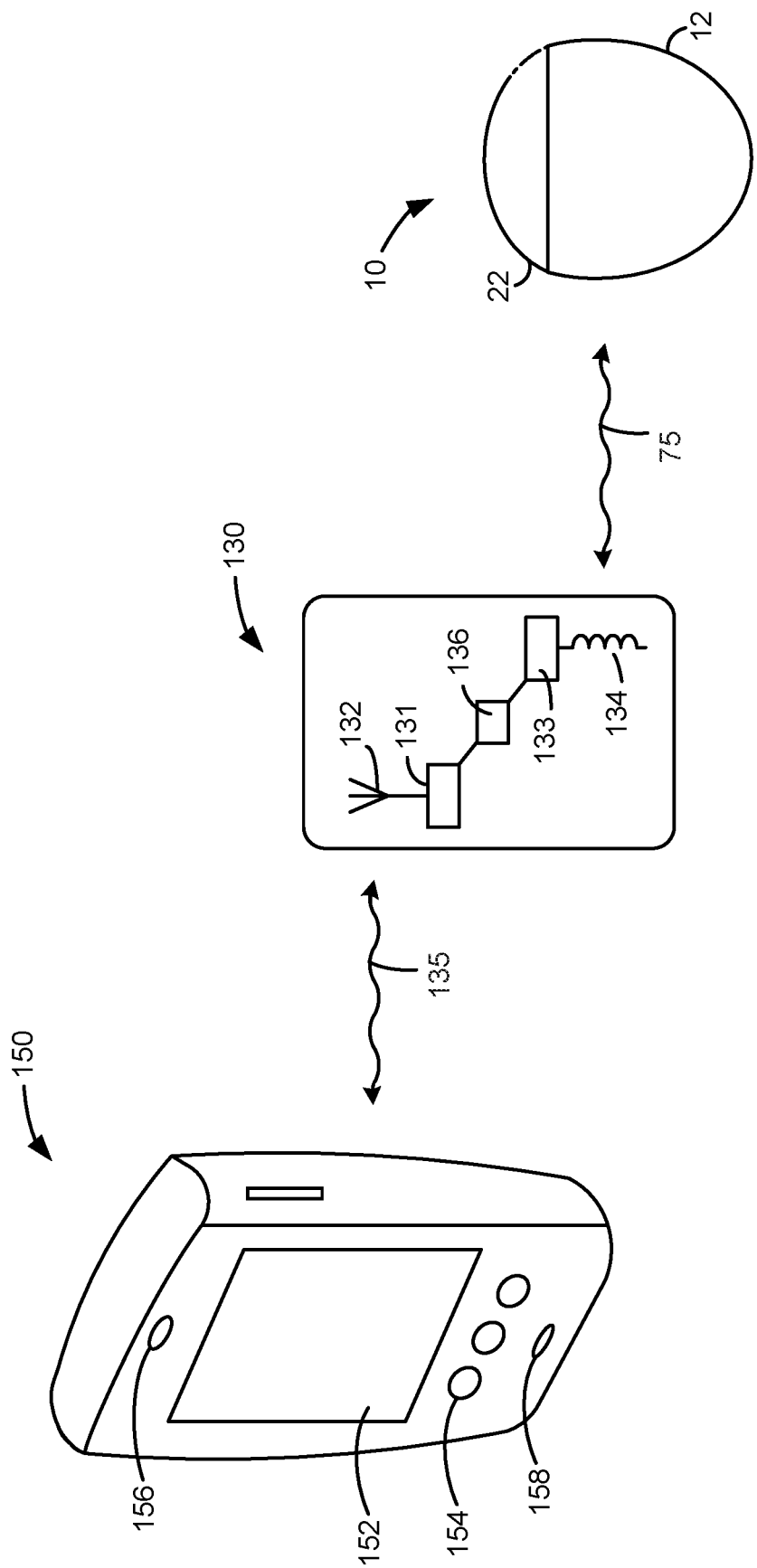

FIG. 4F shows another example of use of a legacy FSK communication link 75 between the mobile device 150 and an (unmodified) IPG 10 (FIG. 2B), in which an intermediary bridge 130 is used, which is disclosed in U.S. Patent Application Publication 2012/0215285, and with which the reader is assumed familiar. The bridge 130 wirelessly communicates with the mobile device 150 via link 135 via a short-range protocol supported by the mobile device, and includes telemetry circuitry 131 and an antenna 132 operable with this short-range protocol. The bridge 130 also wirelessly communicates with the IPG 10 using FSK telemetry via link 75, and includes FSK telemetry circuitry 133 and coil 134. Control circuitry 136 intervenes between the two telemetry circuitries 131 and 133 to control bi-directional communications. Thus, data wirelessly transmitted from the mobile device 150 via link 135 is demodulated at short-range telemetry circuitry 131, and sent to control circuitry 136 which may buffer it, whereafter it is sent to FSK telemetry circuitry 133 where it is modulated and transmitted to the IPG 10 via FSK link 75. Wireless FSK data from the IPG 10 is similarly converted at the bridge 130 to the short-range protocol and transmitted to the mobile device 150 via link 135. In this embodiment, the bridge 130 can be placed proximate to the IPG 10 (such as in a belt with a pocket), while the mobile device 150 can remain relatively distant from the IPG 10 by virtue of the operable distance of the short range protocol in link 135, which again is convenient.

Other means for either directly, or indirectly via an intermediary, enabling communications between a mobile device 150 and an IPG or other implantable medical device could be used as well, and the foregoing means merely provide examples.

Figure 5:
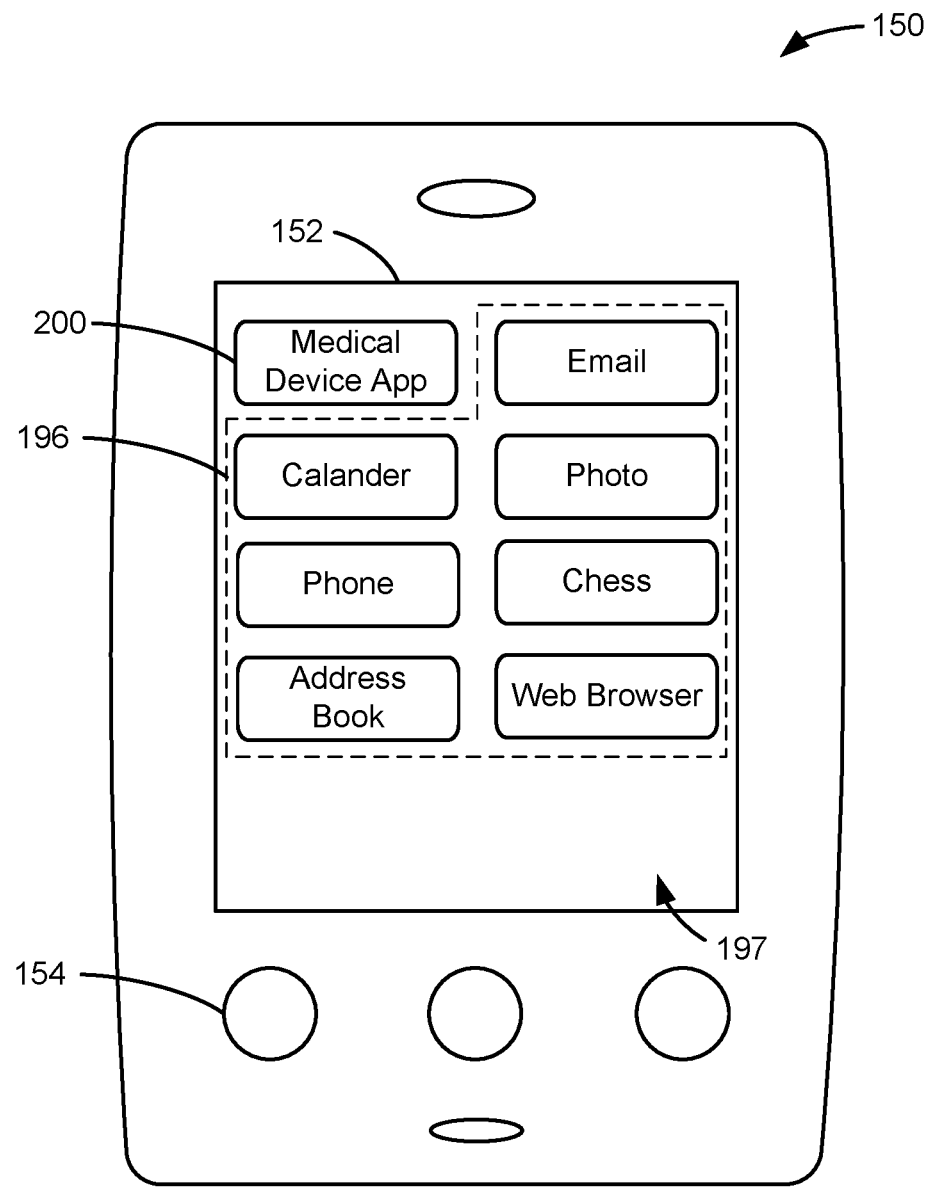
FIG. 5 shows an exemplary manner in which a Medical Device Application (MDA) can be selected via a mobile device graphical user interface.

As shown in FIG. 5, the mobile device 150 can provide a graphical user interface 197, in which a Medical Device Application (MDA) 200 is displayed as an icon and is selectable by the user in typical fashion. Icons for other downloaded applications 196 that the user can select may also be displayed.

Figure 6:
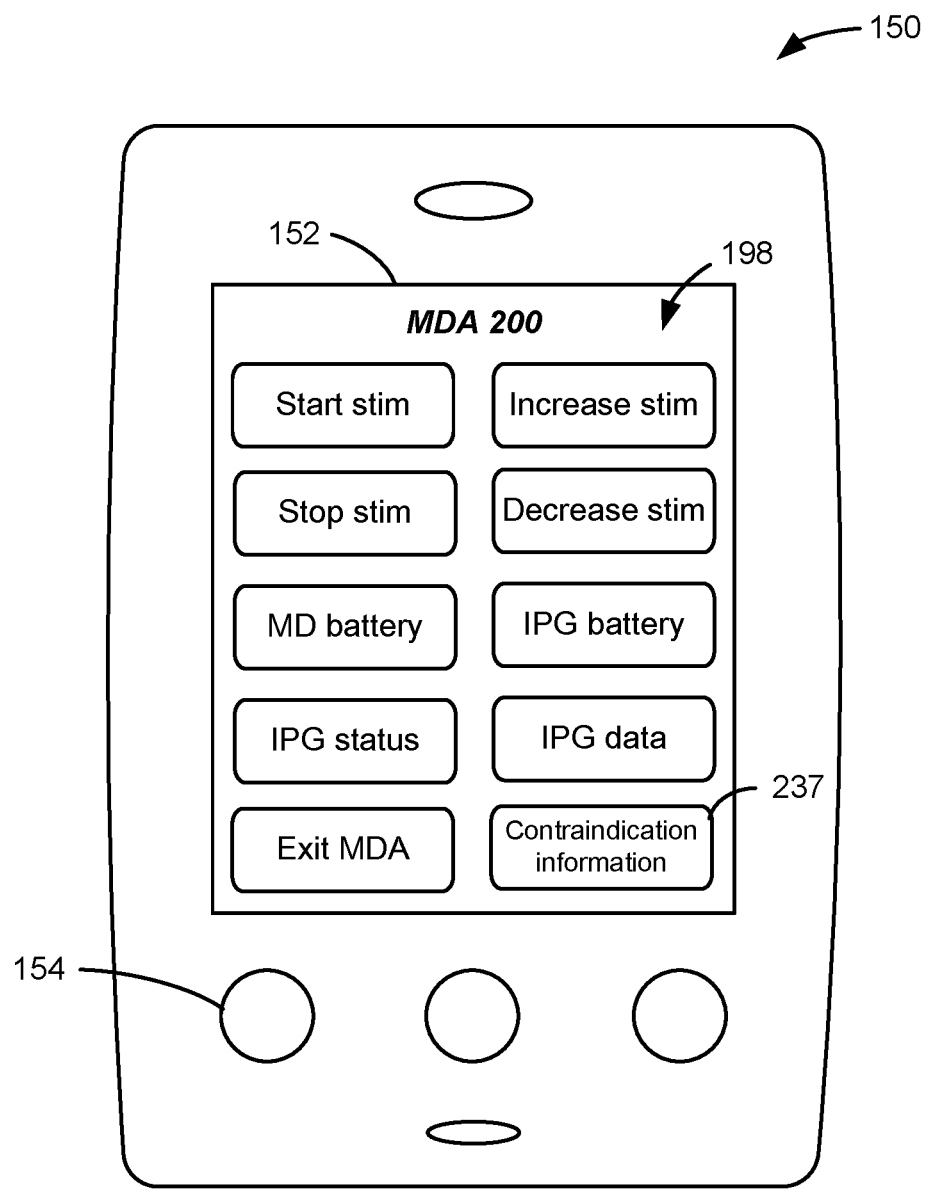
FIG. 6 shows an exemplary graphical user interface for the MDA to enable communications between the mobile device and the IPG.

If MDA 200 is selected and executed, it can provide an MDA graphical user interface 198 to allow a user to send or adjust therapy settings for the IPG and/or to receive data from the IPG, as shown in FIG. 6. For example, the display 152 may present options to start or stop stimulation, to increase or decrease the intensity of stimulation, to check the battery status of the IPG or the mobile device 150, to check the IPG's status, or to review data telemetered from the IPG, etc. Options in either graphical user interface 197 or 198 may be selectable on the display 152 if it is a touch screen, or buttons 154 to allow for user control.

MDA 200 may additionally include a selection 237 to provide contraindication information to the patient, similar to the technique disclosed in U.S. Pat. No. 8,588,925, which is incorporated herein by reference. The '925 patent explains that "contraindication information" can be stored in a traditional dedicated external controller, such as the external controller 50 of FIGS. 2A and 2B, allowing such information to be reviewed on the external controller 50 itself, or provided from the external controller 50 (e.g., by cable, by a memory stick, wirelessly, etc.) to another computer device or system and reviewed there (such as a clinician's computer). Such "contraindication information" can comprise information that a patient or clinician might wish to review when assessing the compatibility of a given therapeutic or diagnostic technique or other activity with the patient's implant, such as: the patient or clinician's manuals for the implant system, including the manuals for the implant and any associated external devices (e.g., remote controllers or external chargers); any specific contraindicated therapeutic or diagnostic techniques or activities; contact information for the manufacturer of the implant system or its service representative; clinician contact information, for example the contact information of the clinician who implanted the implant, or another clinician having information relevant to the use of particular therapeutic or diagnostic techniques or other contraindicated or compatible activities; clinician instructions regarding therapeutic or diagnostic techniques or activities compatible with or contraindicated by the patient's implant; patient history or patient records relevant to a particular therapeutic or diagnostic techniques or activities compatible with or contraindicated by the patient's implant; etc. "Contraindication indication" can also indicate procedures or activities that are compatible with the patient's implant as well as those that are prohibited, at least to some conditional degree. Similar to the teaching of the '925 patent, contraindication information may be stored in the mobile device 150, and via selection 237 may be shown on its display 152 or provided from the mobile device 150 (e.g., wirelessly, using its short-range RF communication means as explained earlier) to another computer device or system.

MDAs can also perform mobile device 150 configuration functions to improve security and to render the mobile device 150 less susceptible to corruption, as explained U.S. Pat. No. 9,186,518, and U.S. Patent Application Publication 2015/0073499, which are incorporated herein by reference.

Figure 7A:
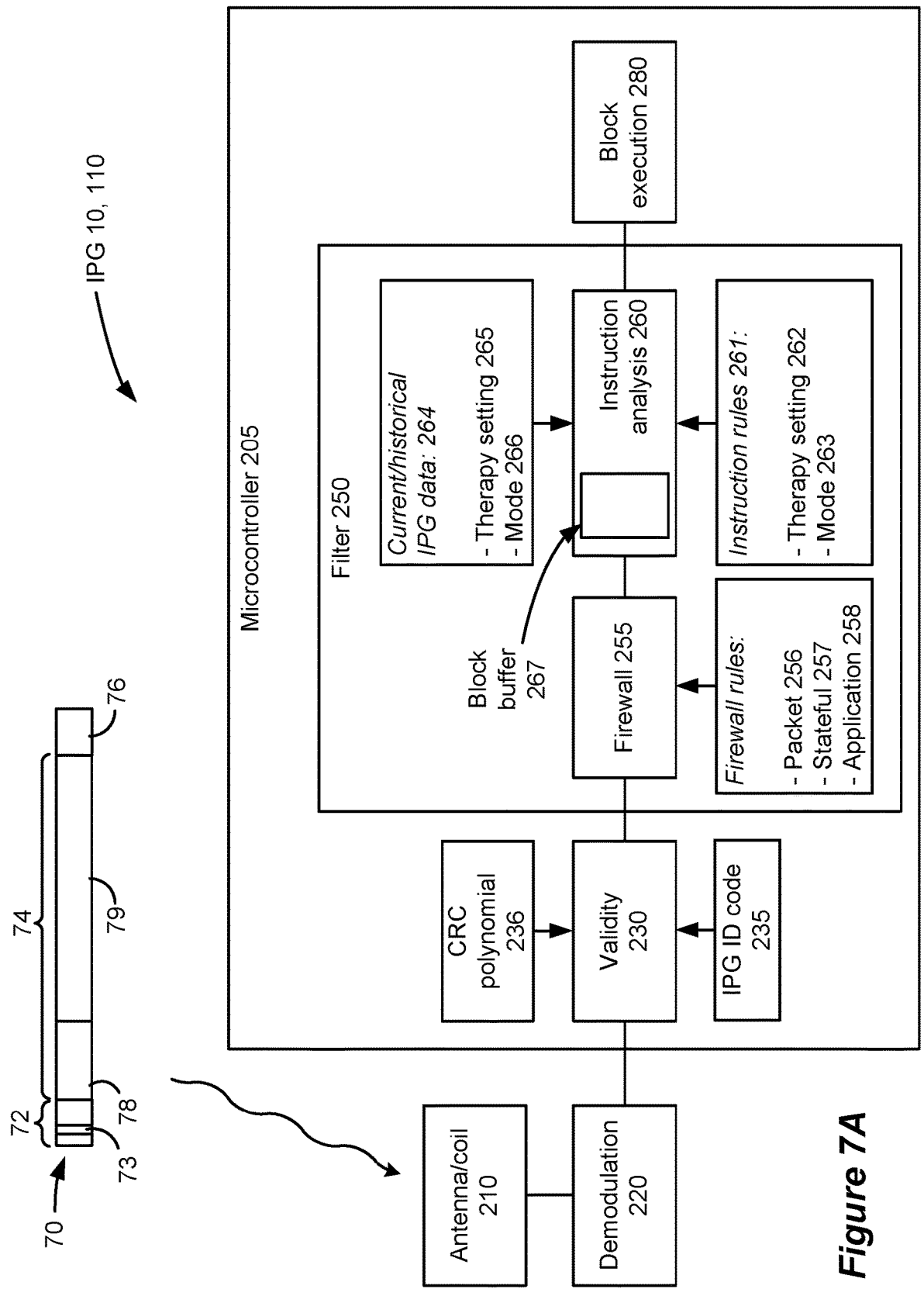
FIG. 7A shows the flow of received blocks through a filter module that implements a filtering algorithm in accordance with an embodiment of the present invention; 7B shows the processing flow of the filtering algorithm.
Figure 7B:
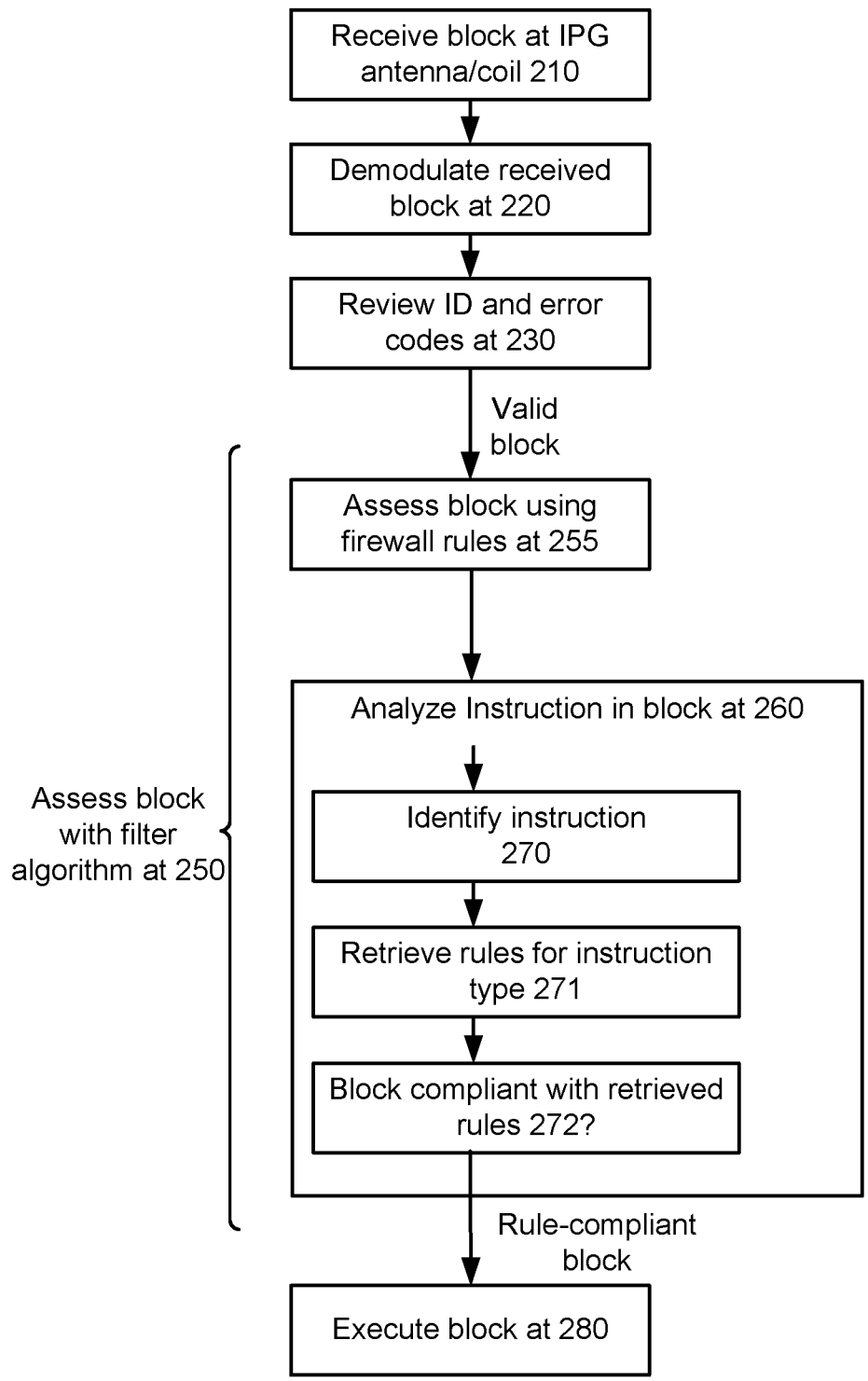
FIG. 7C shows instruction-specific rules that can be provided to an instruction analysis module of the filtering module.

As discussed earlier, implantable medical devices in accordance with another aspect of the invention are programmed with a filtering algorithm to review received blocks before they are executed to change the operation of the implantable medical device. FIG. 7A shows the flow of received blocks through the IPG 10 or 110, including through a filter module that implements the disclosed filtering algorithm, while FIG. 7B shows the processing steps in the filtering algorithm as used in the implantable medical device. These figures are discussed together below.

Blocks 70 are received from the external controller 50, mobile device 150, or other external device (hereinafter, "external device") at the IPG's antenna or coil 210, and are demodulated at a demodulator 220. The IPG antenna 210 and demodulator 220 are designed or chosen to be compliant with the short-range protocol used by the external device to transmit the blocks 70, which as shown in FIGS. 4A-4C can comprise a legacy FSK protocol or other short-range protocol used by the external device as discussed above. The protocol use may define how the blocks 70 are formatted for wireless transmission. For example, if NFC communications are used as described earlier (FIG. 4C), blocks 70 would be formatted in accordance with NFC's Data Exchange Format (NDEF), which is well known. Nonetheless, formats of blocks used in these other short-range protocols generally have the same basic pieces as shown in block 70, and so processing of blocks with this format is described.

Note that a block 70 need not comprise a single data structure transmitted from the external device, but could be transmitted in several smaller units, and then reconstituted at the IPG. A block 70 may also comprise a piece of a larger data structure transmitted by the external device.

The received blocks 70 are preferably provided to a microcontroller 205 in the IPG, and stored in a buffer so that they can be subsequently processed in the correct (e.g., serially-received) order. Microcontroller 205 can comprise a discrete microcontroller or microprocessor integrated circuit, a collection of integrated circuits, a collection of non-integrated circuits, or a collection of both integrated and non-integrated circuits—essentially any hardware capable of processing the received blocks as disclosed herein. Microcontroller 205 can also include memory necessary for its operation, such as ROM or RAM, even if such memory is discrete from the circuitry that processes the blocks 70. Microcontroller 205 would also likely control other or all functions in the IPG in addition to block processing. Various modules in the microcontroller are subsequently explained, and one skilled in the art will understand that these modules can comprise code programmed into the microcontroller 205 to perform their functions. These modules may also contain buffers for the blocks, even if not explicitly discussed. Microcontroller 205 in one example can comprise a Part No. MSP430 microcontroller as described in the data sheet submitted with the Information Disclosure Statement included herewith, and which data sheet is incorporated herein by reference in its entirety.

Once inside the microcontroller 205, the blocks 70 are preferably sent to a validity module 230, which will determine whether a particular block is valid and is allowed to pass for further processing. As discussed in the Background, the validity module 230 preferably determines whether blocks appear to be free of transmission errors (per CRC codes 76), and whether they are intended for the particular IPG (per ID code 73), and are allowed to pass. The CRC polynomial 236 and the IPG's ID code 235 are stored with the microcontroller 205 to assist with these determinations. If a block 70 is invalid because either the ID code check or error code check fails, the IPG can take appropriate action, such as by rejecting the block 70, or requesting the external device to send the block again. Use of validity module 230 is not strictly necessary, or may comprise limited functionality. For example, the validity module 230 may only check error codes 76, or may only check ID code 73 in the blocks. Time stamps may also be appended to the blocks 70 at this point or earlier, which as discussed later can be useful for the filtering algorithm to consider.

Thereafter, valid blocks are passed to a filter module 250 in the microcontroller 205, where the filtering algorithm is performed, and which comprises a firewall module 255 and an instruction analysis module 260. As will be seen below, the firewall module 255 and instruction analysis module 260 provide different means of filtering out and rejecting blocks inconsistent with certain rules. However, while it is preferred to use both modules 255 and 260, benefit is also had by using either alone. While it is further preferred to use the firewall module 255 before the instructions analysis module 260, this is not strictly necessary, and they may instead be used in the opposite order.

The blocks 70 are first presented to the firewall module 255 of the filter module 250, which filters the blocks in light of certain firewall rules to decide whether they should be further processed or should be rejected. Such rules can relate to packet filtering, stateful filtering, or application filtering, and rules for these types of filters 256-258 can be stored with the microcontroller 205 to assist the firewall module 255. The firewall module 255 can implement one, some, or all of these rules.

Packet filtering rules 256 allow the firewall module 255 to inspect headers 72 and filter blocks 70 based on the address (ID code) of the source and the destination (e.g., the external device and the IPG), or ports or services used for communications. Packet filtering rules 256 may also filter blocks 70 based on protocols, the domain name of the source, or other attributes, for example.

Stateful filtering rules 257 monitor handshaking to make sure a communication session is legitimate, and may restrict communications to recognized external devices only.

Application filtering rules 258 (sometimes called proxies) consider the application responsible for the communication, in this case the MDA or other IPG-controlling application, and assess the context of requests and responses to enforce correct application behavior and to block potentially malicious activity. Application filtering can also log activity as well in furtherance of this function.

Use of firewall module 255 is especially useful to protect against traditional attempts to "hack" a patient's IPG, and would, for example, filter out an attempt to "flood" the IPG by sending it large number of blocks. While use of packet, stateful, and application firewalls are known, it should be noted that their incorporation within the IPG itself provides significant benefits, and like the instruction analysis module 260 that follows, provides the IPG with security independent of external factors. This is desirable, as it permits an IPG to be freely used or coupled with external devices regardless whether such external devices themselves are secure.

Blocks 70 not rejected at the firewall module 255 next proceed to an instruction analysis module 260 of the filter module 250. Instruction analysis module 260 analyzes the instructions 78 and data 79 (if present) in each block 70 to determine whether the block, if executed, would violate certain rules 261 that are potentially harmful to the patient and that otherwise would comprise invalid operation of the IPG. If so, the block is rejected and is not executed. Because the rules 261 used by the instructions analysis module 260 are developed to constrain the IPG to safe and sensible operation, the instructions analysis module 260 is in a sense a type of firewall that provides application filtering.

Different rules may be warranted for different instructions 78 in the blocks 70, such as instructions related to setting or adjusting IPG therapy, or instructions related to setting or adjusting an operational mode of the IPG. Accordingly, instruction analysis module 260 identifies the instruction 78 in each block 70 (270; FIG. 7B), and then retrieves at least one rule 261 corresponding to that instruction (271; FIG. 7B). There may be many rules 261 corresponding to a given instruction 78, and a rule 261 may likewise correspond to more than one instruction 78.

FIG. 7C shows some example rules 261 useable by the instruction analysis module 260 that are relevant to instructions that set or adjust therapy 262 and to setting or adjusting the operational mode of the IPG 263. While grouped in this manner for ease of illustration, note that a given rule 261 may be pertinent to therapy setting instructions, IPG mode instructions, or other types of instructions. Moreover, therapy setting rules 262 can depend on the IPG's mode, and IPG mode instructions 263 can depend on IPG therapy settings.

Therapy setting rules 262 prevent the execution of certain therapy settings or therapy setting adjustments, especially if they have potential to injure the patient. For example, the illustrated therapy setting rules 262 prevent the IPG from increasing stimulation: by more than 5% of its current value; by more than 25% over a certain time period (e.g., one minute); or to greater than 15 mA at any electrode. Other therapy setting rules 262 prevent certain decreases in intensity, although as shown in FIG. 7C these rules are not as strict because decreasing stimulation is less worrisome to patient safety. Still other therapy settings rules 262 prevent the frequency and duration of the pulses from being changed by more than a certain percentage, prevent certain changes regarding which electrodes can be activated, and prevent changes to the therapy settings based in the IPG's current mode.

IPG mode rules 263 set rules for how the modes of the IPG can be changed. In one simple example shown in FIG. 7C, an IPG mode rule 263 will not allow the IPG to be placed in a power down mode if the charge of its battery is sufficient for normal operation (e.g., >3.0 V). Other IPG mode rules 263 prevent the entry of certain modes based on other conditions, modes, or therapy settings as shown.

Rules 261 used by the instruction analysis module 260 may be determined based on patient or IPG manufacturer experience as to what constitutes sensible and safe operation of the IPG. Additionally, these rules 261 may be updated. Such updating could occur, for example, when the MDA 200 (FIG. 5) is updated and selected to communicate with the IPG (FIG. 6). If the MDA recognizes that it has received new rules 261 for the instruction analysis module 260, it may automatically send them to the IPG where they are stored with the microcontroller 205. Rules 261 may also be updated under control of a more sophisticated external device, such as a clinician's programmer. Rules 261 may also be updated based on the patient's prior use of the IPG. For instance, in one simple example, if the patient never uses electrode E8 for stimulation, either the external device (which should know the IPG's settings) or the IPG may eventually create a therapy setting rule 262 that electrode E8 should never be activated, as shown in FIG. 7C.

Rules 261 used by the instruction analysis module 260 may also mimic restrictions present in the external device. For example, if the external device (or an MDA 200 operating in the external device; FIG. 6) does not permit a user to increase intensity by more than 5%, a therapy setting rule 262 might reflect this same restriction. Having the rules 261 for instruction analysis module 260 match the restrictions of the changes the external device can make to the IPG is very sensible, because it allows the IPG to reject blocks that are inconsistent with these restrictions, which are likely corrupt.

Once the instruction has been determined (270) and its rules retrieved (271), the instruction analysis module 260 assesses whether the block is compliant with the retrieved rules (272), and whether the block 70 should be rejected or passed on for execution (280). This assessment may consider the data 79 associated with the instruction 78 (if any), and may also depend on the current status of the IPG, e.g., its current therapy settings or its current mode. For example, if the IPG receives an instruction (78) to change intensity to 7 mA (79), the IPG would need to know its current intensity setting to assess compliance with the 5% limitation on intensity increase, or the 20% limitation on intensity decrease, appearing in therapy setting rules 262.

Assessing compliance with rules 261 may further depend on historical data. For example, if the IPG receives an instruction to increase intensity, the IPG intensities used over the last minute would need to be consulted to allow the instruction analysis module 260 to assess compliance with the less-than-25-%-over-one-minute limitation appearing in therapy setting rules 262.

In case such current and historical IPG data 264 is needed by the instruction analysis module, it can be stored with the microcontroller 205 for some reasonable period of time (say 10 minutes), including current and historical therapy setting data 265 and current and historical mode data 266 for the IPG is logged (FIG. 7A), and provided to the instruction analysis module 260. Note that historical current and historical IPG data 264 is preferably time stamped to allow the instruction analysis module 260 to compare the time stamp of the current block 70 under review to time stamps in the historical data, which would be necessary to allow the module 260 to apply the above-noted 25% increase rule for instance.

The IPG may take certain actions if a block is rejected and not executed by the instruction analysis module 260, such as to log the rejected blocks or other information relevant to why the block was rejected, such as which rule 261 was violated. Such logs or other information may be telemetered to the external device for review, which is useful for a number of reasons. First, if a user is sending the rejected block, it is useful to inform the user at the external device that the block has been dropped, so the user can understand that the block was not executed to change IPG operation, at which point that user might try again to send the block. Second, providing rejected-block information to the external device, for example as a report, is useful to allow a user to monitor operation of the filtering algorithm, which might alert the user to potential attempts to tamper with his IPG.

If not rejected, the rule-compliant block 70 is then passed to a block execution module 280 where it is executed by the microcontroller 250 to change operation of the IPG.

Although disclosed to this point as analyzing one block 70 at a time, the instruction analysis module 260 may assess more than one block to make intelligent determinations as to which blocks 70 to pass for execution. In this regard, the instruction analysis module 260 can include a buffer 267 holding numbers of blocks 70 to allow for analysis of those blocks in context of the stream of blocks 270 received by the IPG. The buffer 267 may hold in addition to the current block under review at least one previously-received block, at least one subsequently-received block, or both, and can analyze the current block in light of such other blocks.

Such multiple-block assessment by the instruction analysis module 260 may consider the timing with which the blocks 70 are received, and as noted earlier the blocks may be time-stamped prior to their arrival in the filtering module 250. Such multi-block review at instruction analysis module 260 is useful to ensure that blocks do not radically change therapy or IPG operation, particularly on short time scales that likely do not reflect user selections at the external device. Note that multi-block review may cause blocks 70 to be delayed in their execution, as compliant blocks may need to be held in the buffer 267 to allow for review of subsequent blocks, but keeping blocks in the buffer for only a small maximum amount of time (e.g., 1 second) would probably not be noticeable by the user. Multi-block review may cause the instruction analysis module 260 to reject either a single block or number of blocks in its buffer 267 that violate a particular rule 261.

Simple examples of some rules 261 that are used when the instruction analysis module 260 reviews numbers of received blocks in context are shown in bold in FIG. 7C. For example, assume the instruction analysis module 260 receives a block 70 comprising a change to frequency or duration. As well as reviewing the current block individually to see if it violates the 10% change limitation, the instruction analysis module 260 may also review the succeeding later-received block in its buffer 267 to see if that block comprises an instruction to change intensity. As shown, a therapy setting rule 262 prohibits the frequency or duration adjustment in this instance, presumably because it views changing the frequency or duration and intensity in short succession as too radical of a therapy change, and hence a change that a user is not likely to make. Note that this rule essentially also prioritizes the later-received intensity instruction over earlier-received frequency/duration instruction. Alternatively, the instruction analysis module 260 upon review of the frequency/duration instruction may give priority to the earlier-received frequency/duration instructions and decide to reject the intensity instruction, even before it is individually reviewed for rule compliance. Or, the instruction analysis module 260 could simply drop both blocks and prevent both from execution.

Another therapy setting rule 262 prohibits a block increasing intensity if any preceding earlier-received block in the buffer 267 received 0.5 seconds earlier would decrease intensity, which may be accomplished by review of time stamps of the blocks. Again, the instruction analysis module 260 could prioritize execution of these two blocks differently while still in the buffer 267, and could handle the conflict earlier upon reviewing the earlier-received decrease instruction individually. Again, both blocks might alternatively be dropped.

Another therapy setting rule 262 considers any therapy setting instruction, and considers whether any preceding earlier-received block in the buffer 267 comprises an instruction to place the IPG in a program mode in which it readies itself for new programming data (e.g., a software update) from the external device. Here, the timing of receipt between the therapy setting instruction and the program mode instruction does not matter (so long as the program mode instruction is still in the buffer 267), and hence review of time stamps of the blocks would not be necessary. Again, the instruction analysis module 260 upon earlier review of the program mode instruction (per an IPG mode rule 263) could preemptively reject all blocks containing therapy setting instructions in its buffer 267 prior to execution of the program mode instruction.

An example multi-block rule 263 related to an IPG mode instruction is also shown in bold in FIG. 7C, namely that a block containing a mode change will not be executed if a preceding and succeeding block in the buffer 267 within 0.5 second comprises a therapy setting instruction. The rationale for this rule 263 may be that it would be unusual for a user to make an IPG mode change so quickly between therapy adjustments. The instruction analysis module 260 might thus view this circumstance as peculiar and not likely requested the user, and therefore reject the IPG mode instruction.

An IPG need not use all aspects of the filter module 250 at all times. For example, if the IPG recognizes that it is receiving communications from a secure external device such as a clinician's programmer, the IPG may disable either the firewall module 255 or the instruction analysis module 260, or both.

Figure 8A:
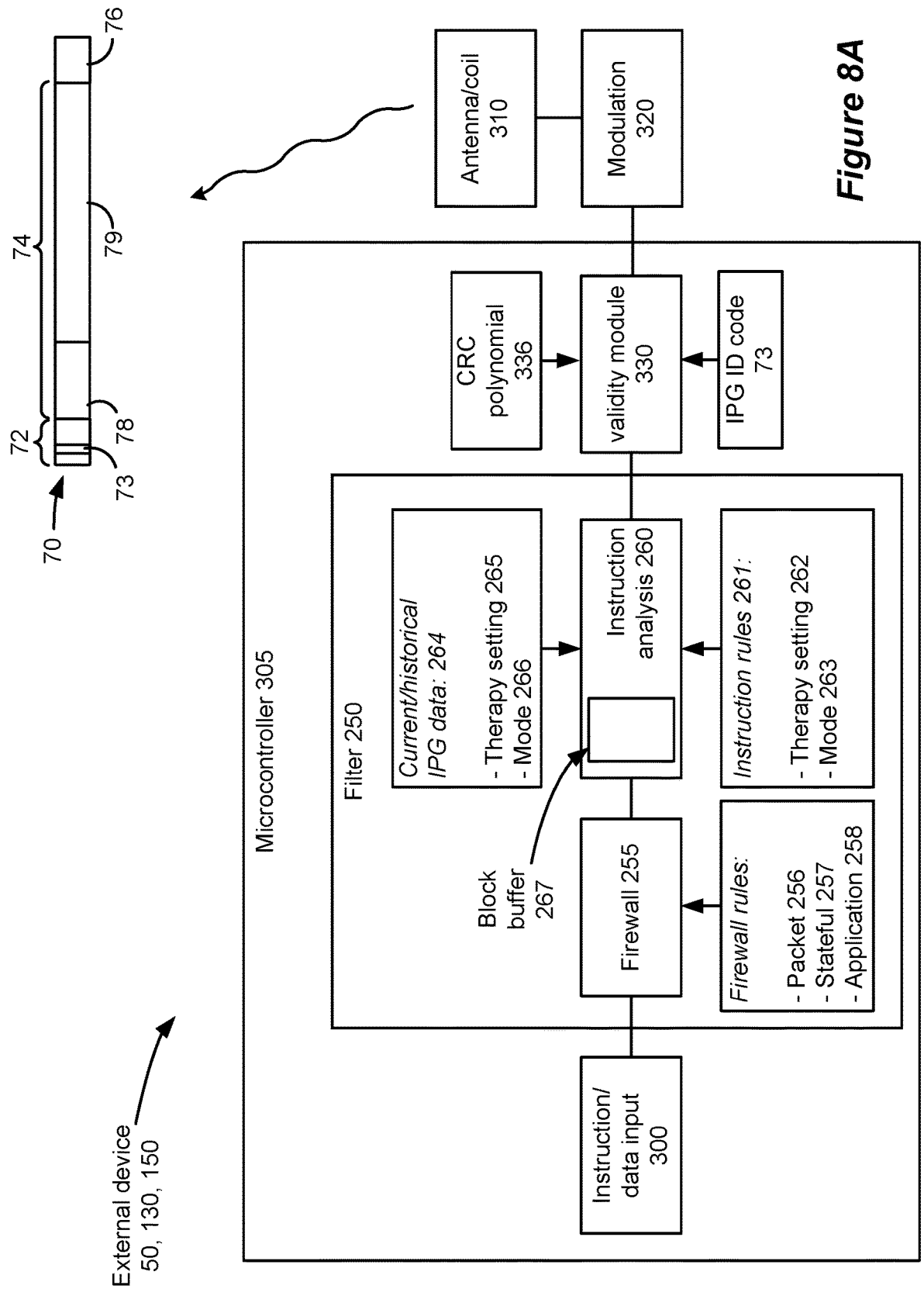
FIGS. 8A and 8B shows use of the filtering algorithm in an external device, such as mobile device, a legacy external controller, or a bridge device.
Figure 8B:
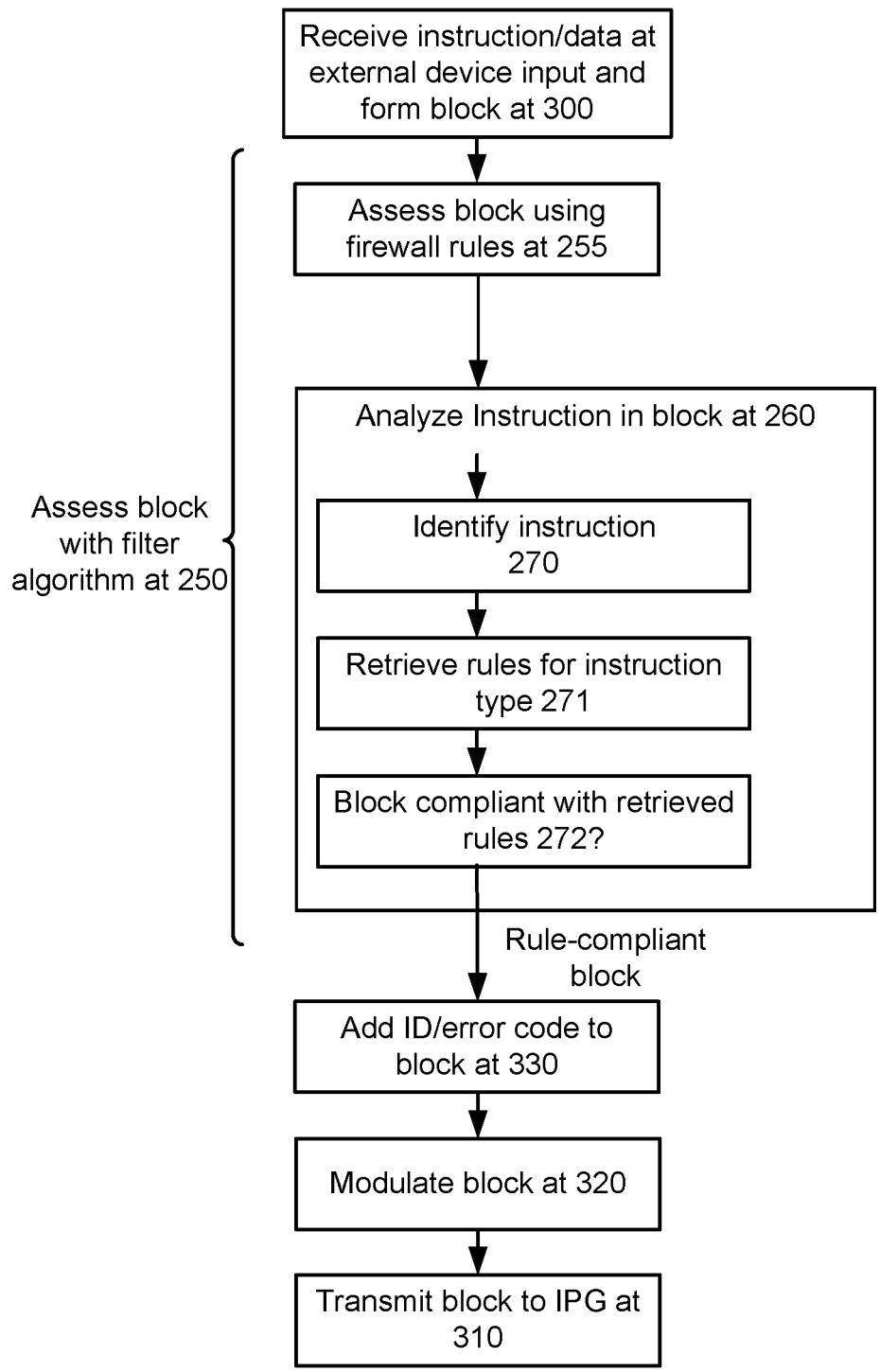

Although use of the filtering algorithm in an IPG or other implantable medical device has been illustrated to this point, the filtering algorithm can be used in external devices that communicate with the IPG as well, as shown in FIGS. 8A and 8B. Such external devices employing the filtering algorithm could comprise mobile devices 150 (FIG. 4A), legacy external controllers 50 (FIG. 2A), bridge devices 130 (FIG. 4F) between the external device and the implant, or any other external device capable of communicating with the IPG. Use of the filtering algorithm in an external device provides essentially the same security benefits as disclosed earlier with respect to use in an implantable medical device, albeit on the sending side of the communication link. Moreover, the filtering algorithm could be used in both the external device and the implantable medical device.

FIG. 8A shows the flow of blocks through the external device, including through the filter module 250 that implements the disclosed filtering algorithm, while FIG. 8B shows the processing steps in the filtering algorithm as used in the external device. These figures are discussed together below. Much of the circuitry and steps in FIGS. 8A and 8B match corresponding blocks or steps in FIGS. 7A and 7B, perhaps as modified given the external device's role as a sending device for the blocks 70.

As shown, the external device receives instructions and possibly associated data at an input 300. Such input can occur in different manners depending on the external device. For example, if the external device is a mobile device 150 or legacy external controller 50, the input may come from a user interface of those devices, with the instructions/data comprising therapy settings or adjustments, IPG mode selections, etc., as described previously. Or the input may be wirelessly received at the external device, as would occur were the external device a bridge device 130 receiving the instructions/data from another external device such as a mobile device 150 which is used to communicate with the IPG via the bridge 130 as described earlier (FIG. 4F). Once the instructions/data are input, they are formatted as blocks 70.

The block 70 can next be sent to the filter module 250 in the external device, where the disclosed filter algorithm is performed to pass or reject blocks. This may occur as described earlier in the IPG (FIGS. 7A and 7B), with either or both of the firewall module 255 and the instruction analysis module 260 operating to assess the blocks based on a number of rules (256-258, 262-263). Operation and functionality of these modules 255 and 260 is not repeated.

The external device may not have access to current or historical IPG data 264, in which case the instruction analysis module 260's instruction rules 261 would be modified to exclude rules reliant upon such data 264. However, such current or historical IPG data 264 can also be sent to the external device for use in the instruction analysis module 260, such as by using the technique described in U.S. Provisional Patent Application Ser. No. 61/873,314, filed Sep. 3, 2013, which is incorporated herein by reference, and which discusses how IPG log data can be sent to an external device and maintained in a file at the external device for use by an Medical Device Application such as MDA 200 discussed earlier.

If the blocks 70 are compliant with the rules at the filter module 250, they are allowed to pass to a validity module 330, which appends an ID code 73 to each block, and/or determines an error code 76 for each block in conjunction with a CRC polynomial 336, which error code 76 is then appended to each block, as described earlier. Use of the validity module 330 can also precede use of the filter module 250, or may be omitted. Thereafter, compliant blocks 70 are modulated 320 and transmitted to the IPG via an antenna 310 in the external device.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
a plurality of electrodes selectable to provide stimulation to a patient's tissue; and
control circuitry that is programmed with a filter module comprising a plurality of instruction rules that each specify a type of therapy setting or operational mode setting for the implantable medical device, wherein the filter module, when enabled, is configured to:
receive an instruction from an external device; and
execute the instruction to change the stimulation provided at the plurality of electrodes or to change an operational mode of the implantable medical device only if it is determined that the instruction is compliant with the one or more instruction rules,
wherein the control circuitry is configured to disable the filter module upon determining that the instruction is received from a clinician programmer as the external device.

2. The implantable medical device of claim 1, further comprising an antenna and demodulation circuitry configured to wirelessly receive and demodulate the instruction from the external device in accordance with a short-range communication protocol, and configured to provide the instruction to the control circuitry.

3. The implantable medical device of claim 2, wherein the short-range communication protocol comprises a Near Field Communication (NFC) protocol.

4. The implantable medical device of claim 2, wherein the short-range communication protocol comprises a Frequency Shift Keying (FSK) protocol.

5. The implantable medical device of claim 2, wherein the short-range protocol comprises a Bluetooth, Bluetooth Low Energy (BLE), Zigbee, or WiFi protocol.

6. The implantable medical device of claim 1, wherein at least one of the instruction rules specifies a percentage change in stimulation amplitude.

7. The implantable medical device of claim 1, wherein at least one of the instruction rules specifies a percentage change in stimulation amplitude in a period of time.

8. The implantable medical device of claim 1, wherein at least one of the instruction rules specifies a percentage change in stimulation frequency.

9. The implantable medical device of claim 1, wherein the filter module further causes the control circuitry to retrieve the one or more instruction rules that are associated with the identified instruction.

10. The implantable medical device of claim 1, wherein the control circuitry is configured to store time-stamped current and historical settings of the implantable medical device.

11. The implantable medical device of claim 10, wherein the filter module determines whether the instruction complies with at least one of the one or more instruction rules by evaluating the instruction and one or more of the time-stamped current or historical settings of the implantable medical device.

12. The implantable medical device of claim 1, wherein the control circuitry comprises a buffer that is configured to store the received instruction along with instructions previously received from the external device, instructions subsequently received from the external device, or both.

13. The implantable medical device of claim 12, wherein the control circuitry is configured to time stamp the instruction received from the external device.

14. The implantable medical device of claim 13, wherein the filter module determines whether the instruction complies with at least one of the one or more instruction rules by evaluating the instruction and one or more instructions stored in the buffer.

15. A method implemented in an implantable medical device comprising a plurality of electrodes selectable to provide stimulation to a patient's tissue, the method comprising:
enabling a filter module in control circuitry in an implantable medical device, wherein the filter module is programmed with a plurality of instruction rules that each specify a type of therapy setting or operational mode setting for the implantable medical device;
receiving an instruction from an external device;
determining using the control circuitry whether the external device is a clinician programmer, and if so, disabling the filter module; and
if the external device is not determined to be a clinician's programmer, using the filter module to execute the instruction to change the stimulation provided at the plurality of electrodes or to change an operational mode of the implantable medical device only if it is determined that the instruction is compliant with the one or more instruction rules.

16. The method of claim 15, wherein the instruction is received at an antenna in the implantable medical device, and further comprising demodulating the instruction in accordance with a short-range communication protocol.

17. The method of claim 15, wherein at least one of the instruction rules specifies a percentage change in a stimulation parameter.

18. A non-transitory computer readable medium containing instructions executable in control circuitry of an implantable medical device comprising a plurality of electrodes selectable to provide stimulation to a patient's tissue, wherein the instruction when executed are configured to:
enable a filter module in the control circuitry, wherein the filter module is programmed with a plurality of instruction rules that each specify a type of therapy setting or operational mode setting for the implantable medical device;
receive an instruction from an external device;
determine whether the external device is a clinician programmer, and if so, disabling the filter module; and
if the external device is not determined to be a clinician's programmer, use the filter module to execute the instruction to change the stimulation provided at the plurality of electrodes or to change an operational mode of the implantable medical device only if it is determined that the instruction is compliant with the one or more instruction rules.

* * * * *